United States Patent
Kammerer et al.

[11] Patent Number: 6,156,044
[45] Date of Patent: *Dec. 5, 2000

[54] MENISCAL REPAIR DEVICE

[75] Inventors: Gene W. Kammerer, East Brunswick; Susan Trenka-Benthin, Pennington; Keith Seritella, Kendall Park; Rupam Naik, Bridgewater, all of N.J.

[73] Assignee: Ethicon, Inc., Somerville, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/358,069

[22] Filed: Jul. 21, 1999

Related U.S. Application Data

[63] Continuation of application No. 08/766,535, Dec. 11, 1996.

[51] Int. Cl.$^7$ .................................................. A61B 17/04
[52] U.S. Cl. ............................................................ 606/144
[58] Field of Search .................................. 606/144, 148, 606/221, 222, 224, 227

[56] References Cited

U.S. PATENT DOCUMENTS

| | | |
|---|---|---|
| 4,006,747 | 2/1977 | Kronenthal et al. ................ 606/144 X |
| 5,007,921 | 4/1991 | Brown . |
| 5,290,296 | 3/1994 | Phillips . |
| 5,474,557 | 12/1995 | Mai . |

*Primary Examiner*—Michael Buiz
*Assistant Examiner*—Vikki Trinh
*Attorney, Agent, or Firm*—Emil Richard Skula

[57] ABSTRACT

An H-type fastener for surgical tissue. The fastener has a central biasing member. The biasing member has a first end and a second end. Anchor members are mounted to each end.

3 Claims, 10 Drawing Sheets

FIG. 13
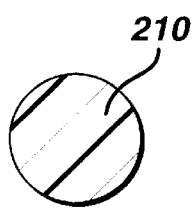
FIG. 17
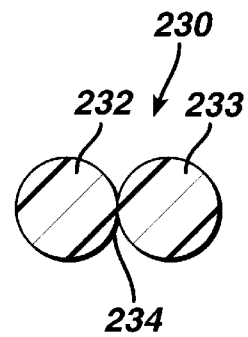
FIG. 14
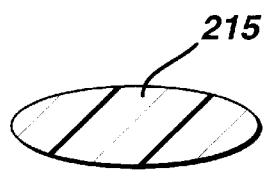
FIG. 18
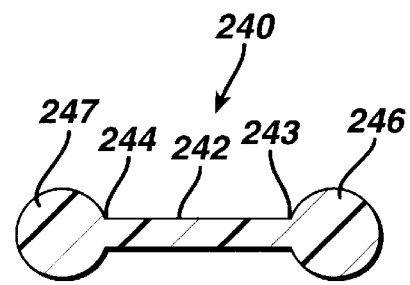
FIG. 15
FIG. 19
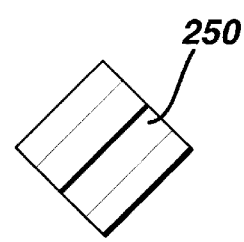
FIG. 16
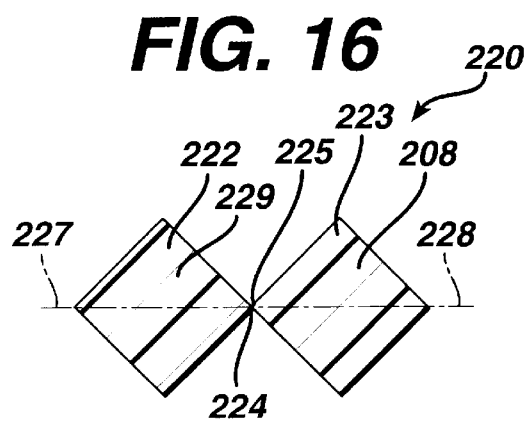
FIG. 20
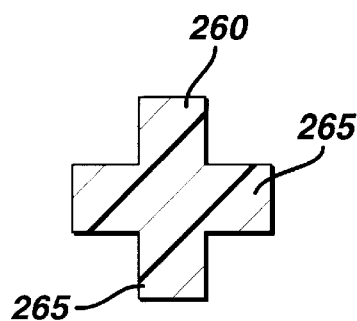

MENISCAL REPAIR DEVICE

This application is a continuation of Ser. No. 08/766,535 filed Dec. 11, 1996.

TECHNICAL FIELD

The field of art to which this invention relates is medical devices for tissue approximation, in particular, medical devices for approximating soft tissue.

BACKGROUND OF THE INVENTION

Recent advances in minimally invasive surgical techniques, such an endoscopy, laparoscopy and arthroscopy, have made it possible for complex surgical techniques to be performed with minimal disruption and cutting of tissue. These techniques are performed using various types of scopes which allow the surgeon to visualize the operative site. The scopes and instruments are designed to be inserted through trocar cannulas which are positioned about the operative site using trocar knives or obturators. The trocar obturators produce minimal punctures when inserted into a body cavity or joint. The body cavity or joint is typically insufflated or expanded with a biocompatible gas or liquid, such as carbon dioxide or sterile saline solution in order to provide the surgeon with room to conduct the surgical procedure.

In most surgical procedures, tissue must be approximated to repair wounds and tears and to close incisions. There are numerous known methods and devices for approximating tissue. The devices include surgical needles, surgical sutures, staples and the like. It is also known to use surgical tacks and other fasteners. One particular type of fastener which is known is an "H-shaped" fastener. H-type fasteners and methods of use are disclosed in U.S. Pat. Nos. 4,006,747 and 4,586,502 which are incorporated by reference. The H-type fastener typically has a central connecting section having opposed ends with tissue anchor members mounted to each end. H-type fasteners and fastening systems for non-medical use are commonly used to affix labels and tags to clothing.

The H-type fasteners may have advantages over conventional fasteners in certain minimally invasive techniques. In particular, it is known to use H-type fasteners in arthroscopic techniques such as meniscal repair as disclosed in U.S. Pat. No. 5,320,633. Damage to the meniscus, such as rips or tears, has been found to be repairable if the torn pieces of the meniscus are approximated. At one time, the prevailing practice was such that the torn sections of the meniscus would be surgically removed, eventually resulting in damage to the bones in the joint caused by bone-on-bone contact. Presently, however, it has been found that, in order for the meniscal repair to be effective, the opposing surfaces of the torn or ripped meniscus must be approximated such that the surfaces are maintained in close contact.

The H-type fasteners are believed to be effective in meniscal repair since they are relatively easy to insert using a conventional apparatus having a cannulated distal needle wherein the needle has a longitudinal slot. One leg or tissue anchor of the H-type fastener is loaded into the cannulated needle, preferably having a slot. The needle is inserted through both sides of the meniscal tear and one leg or anchor is expelled from the needle on one side of the tear. The needle is then removed from the meniscus and the other opposed leg or anchor remains in place positioned on the opposite side of the tear, thereby approximating the meniscal tear.

There are certain disadvantages associated with the use of existing H-type fasteners to approximate a tear in a meniscus. One disadvantage is that the surgeon must precisely measure the meniscus prior to inserting the H-type fastener in order to select the proper size H-type fastener. A precise measurement is necessary because the fastener must be sized to approximate and compress the opposing sides or surfaces of the tear against each other. One skilled in the art will appreciate the difficulties involved in attempting to obtain such measurements during an arthroscopic or minimally invasive procedure in which a scope is used. Even if a precise measurement is possible and an appropriately sized H-type fastener is utilized, proper tissue approximation is difficult to accomplish since it is often impossible to precisely place a needle in a meniscus, in vivo, especially during an arthroscopic procedure. Consequently, the meniscus is often under-approximated with inadequate face-to-face contact, or over-approximated with inadequate face-to-face contact. In addition, there are only a limited number of sizes of H-type fasteners which the surgeon will typically have available during an operative procedure, further complicating the surgical procedure and the obtention of adequate tissue to tissue contact in the repaired meniscus. As alluded to above, the surgeon must precisely choose the size of the H-type fastener. If the H-type fastener selected by the surgeon is too large, there will be no tissue approximation. If the H-type fastener is too small, the tissue may fold and bunch, possibly turning the edges or surfaces of the tear so that they are not in contact with each other, thereby effecting only a partial or inadequate repair.

What is needed in this art are improved H-type surgical fasteners for approximating tissue which overcome the disadvantages associated with the H-type fasteners of the prior art.

DISCLOSURE OF THE INVENTION

It is an object of the invention to provide an H-type fastener having a biasing section which, when inserted through two adjacent sections of body tissue, causes the edges or surfaces of the tissue to compress against each other.

It is yet another object of the present invention to provide an H-type fastener which eliminates or minimizes the need to make precise in-vivo measurements of tissue prior to insertion.

It is still yet a further object of the present invention to provide a method of surgically approximating tissue using an H-type fastener having a biasing section, said biasing section providing a biasing force to maintain the edges or surfaces of tissue about a tear approximated.

Accordingly, an H-type fastener is disclosed. The H-type fastener has a central elongated biasing member having a first end and a second end. Mounted to the first end of the biasing member is a first tissue anchor. Mounted to the second end of the biasing member is a second tissue anchor. The elongated biasing member has a resting position, and may be elastically deformed to an extended position. In the extended position, the biasing member exerts a biasing force. The biasing member may have various resting position configurations including saw tooth waves, sine waves, helixes, arcs, parabolas, combinations of straight and curved sections, and the like. The tissue anchors may similarly have a variety of configurations and may be rod-shaped, disk-shaped, spherical, etc.

Yet another aspect of the present invention is an H-type fastener. The H-type fastener has an elongated central connecting member having a first end and a second end. Mounted to the first end of the central member is a first biasing tissue anchor. Mounted to the second end of the connecting member is a second biasing tissue anchor. The biasing tissue anchors have a first resting configuration and a second elastically deformed configuration. When elastically deformed, the tissue anchors exert a biasing force.

Yet another aspect of the present invention is a method of approximating tissue using the tissue approximating devices of the present invention. The method consists of inserting an H-type fastener of the present device having a central biasing section into tissue. Next, one tissue anchor is moved to a first position in or about the tissue, and the second anchor is moved to a second position in or about the tissue such that the biasing section is elastically displaced from its resting position to an extended position, thereby causing tissue between the anchors to be approximated and causing a biasing force to be exerted upon the tissue.

Still yet another aspect of the present invention is a method of approximating tissue using the tissue approximating devices of the present invention. The method consists of inserting an H-type fastener of the present device having biasing tissue anchors and a non biasing central member into tissue. Next, one biasing tissue anchor is moved to a first position in or about the tissue, and the biasing second anchor is moved to a second position in or about the tissue such that the biasing tissue anchors are elastically displaced from their resting positions to extended positions, thereby causing tissue between the anchors to be approximated and causing a biasing force to be exerted upon the tissue. The biasing anchors may also have a variety of configurations including V-shaped, X-shaped, etc.

These and other aspects of the present invention will become more apparent from the following description and accompanying drawings.

BRIEF DESCRIPTION OF THE DRAWINGS

FIG. 13 is a cross-section of a biasing section of an H-type fastener of the present invention having a circular configuration.

FIG. 14 is a cross-section of a biasing section of an H-type fastener of the present invention having an elliptical configuration.

FIG. 15 is a cross-section of a biasing section of an H-type fastener of the present invention having a rectangular configuration.

FIG. 16 is a cross-section of a biasing section of an H-type fastener of the present invention having a configuration consisting of two squares, each joined together diagonally at a corner.

FIG. 17 is a cross-section of a biasing section of an H-type fastener of the present invention having a configuration having two circles tangentially connected.

FIG. 18 is a cross-section of a biasing section of an H-type fastener of the present invention having a configuration consisting of a rod with a circle at each end.

FIG. 19 is a cross-section of a biasing section of an H-type fastener of the present invention having a square configuration.

FIG. 20 is a cross-section of a biasing section of an H-type fastener of the present invention having a cross configuration.

DESCRIPTION OF THE PREFERRED EMBODIMENTS

The H-type fasteners of the present invention may be made from numerous conventional biocompatible polymers. The biocompatible polymeric materials can be either conventional non-absorbable biocompatible polymeric materials, or conventional absorbable or resorbable biocompatible polymeric materials. Examples of the non-absorbable biocompatible materials which can be used include polypropylene, nylon, polyethylene, polyester polyolefin and the like and equivalents thereof. The conventional absorbable and resorbable biocompatible polymeric materials which can be used to manufacture the H-type fasteners of the present invention include polydioxanone, polygalactic acid, polylactic acid, polycaprolactone, copolymers and blends thereof as well as equivalents thereof. The polymers may be mixed with bone growth enhancing materials such as calcium hydroxyapatite and the like. Examples of some of the foregoing materials are contained in U.S. Pat. No. 4,052,988 and U.S. Pat. No. 5,252,701. Although not particularly preferred, those skilled in the art will appreciate that the H-type fasteners of the present invention may be manufactured from other conventional types of biocompatible materials including metals such as stainless steel spring steel and nickel-titanium alloys, ceramics, composites, and the like and equivalents thereof. The H-type fasteners of the present invention may be manufactured using conventional manufacturing processes. For example, when manufacturing the fasteners of the present invention the following processes, among others, may be used: injection molding, insert molding, extrusion molding, thermal bonding, solvent bonding, annealing, heat treatment, mechanical deformation, heat fusion, welding, machining cutting, etc.

Figure 2:
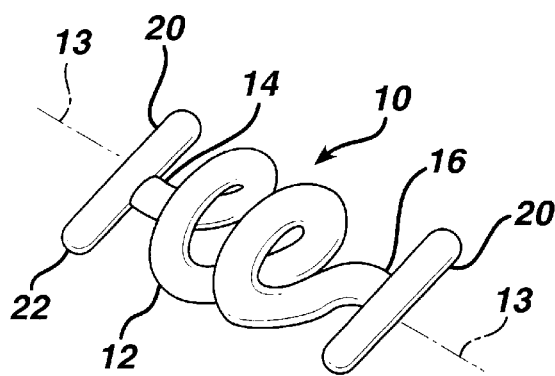
FIG. 2 is a perspective view of an H-type fastener of the present invention having a helical biasing section.
Figure 2A:
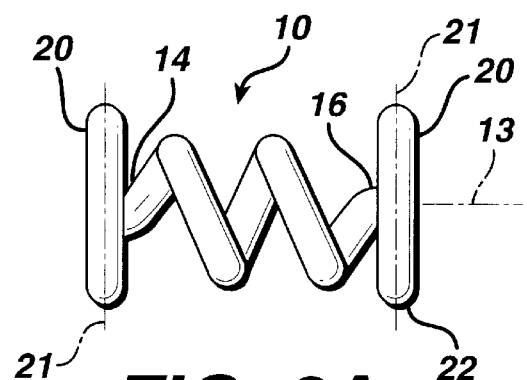
FIG. 2A is a side view of the H-type fastener of FIG. 2.

Referring now to FIG. 2, a preferred embodiment of an H-type fastener 10 of the present invention is illustrated. The fastener 10 is seen to have central helically-shaped biasing section 12 having first and second ends 14 and 16. Biasing member 12 is also seen to have central longitudinal axis 13. Mounted to the ends 14 and 16 of the biasing member 12 are the tissue anchors 20. As seen in FIG. 2, tissue anchors 20 are substantially rod-shaped members having opposed rounded ends 22, although anchors 20 may have other configurations. e.g., spheres, discs, beams, etc. The ends of anchors 20 may also be pointed, flat, conical, pyramidal, etc. The tissue anchors 20 are seen to have longitudinal axes 21. The tissue anchors 20 are mounted to the ends 14 and 16 of the biasing member 12 such that the longitudinal axes 21 of the tissue anchors 20 are substantially perpendicular to the longitudinal axis 13 of the biasing member 12. The anchors 20 are also seen to be centrally mounted to the ends 14 and 16. The axes 21 may be parallel or may be angulated with respect to each other or rotated with respect to each other. An elongation of biasing member 12 from a normal resting position to and extended position will result in a biasing force being placed upon tissue by anchor members 20 such that when the device 10 is placed into tissue and the biasing member 10 is elongated, the tissue between anchor members 20 will be compressed as a result of the biasing force exerted upon anchor members 20 by biasing member 12.

Figure 1:
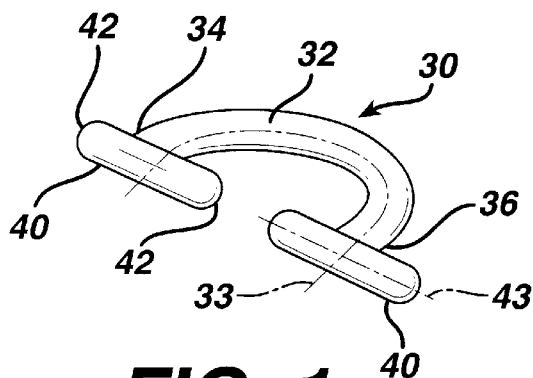
FIG. 1 is a perspective view of an H-type fastener of the present invention having a semicircular biasing section.
Figure 1A:
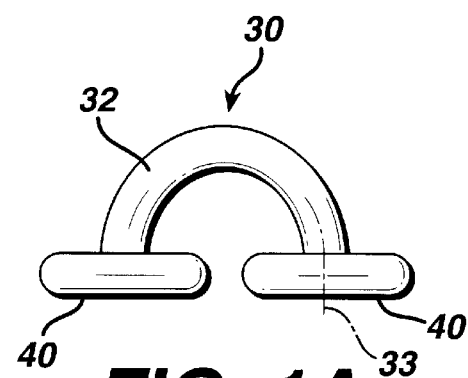
FIG. 1A is a side view of the H-type fastener of FIG. 1.

Another embodiment of an H-type fastener of the present invention is seen in FIGS. 1 and 1A. The H-type fastener 30 illustrated in FIGS. 1 and 1A is seen to have central biasing member 32 having longitudinal axis 33. Central biasing member 32 is seen to have a semicircular configuration with an approximately 180 degree arc, although arcs of lesser magnitude may be used. The biasing member 32 is seen to have longitudinal axis 33 and first end 34 and second end 36. Mounted to the first and second ends 34 and 36 of the biasing member 32 are the tissue anchors 40. The tissue anchors 40 are seen to be substantially rod-shaped members having rounded ends 42 and longitudinal axes 43. The rod-shaped anchors 40 are centrally mounted to the ends 34 and 36 such that the longitudinal axes 43 of the anchor members are substantially perpendicular to the longitudinal axis 33 of biasing member 32 at the ends 34 and 36. If desired, the rod-shaped tissue anchors 40 may be mounted in such a manner that their longitudinal axes 43 are angulated with respect to each other, for example, at 45°, or are rotated with respect to each other, for example, at 90° so that the axes 43 of tissue anchors 40 are not in the same plane.

Figure 3:
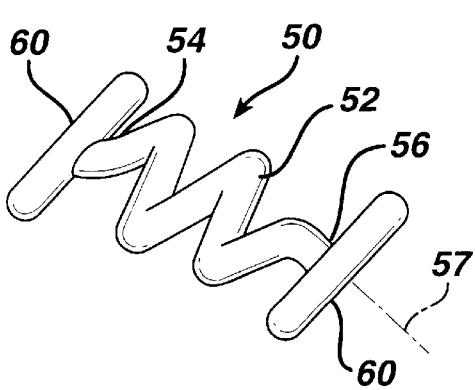
FIG. 3 is a perspective view of an H-type fastener of the present invention having a biasing section with a saw-tooth configuration.
Figure 3A:
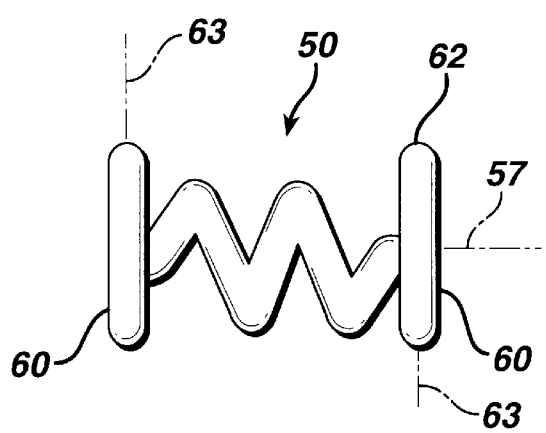
FIG. 3A is a side view of the H-type fastener of FIG. 3.

FIGS. 3 and 3A illustrate yet another embodiment of the H-type fasteners of the present invention. The fastener 50 is seen to have central biasing section 52 having first and second ends 54 and 56 respectively. The biasing member 52 is seen to have longitudinal axis 57. Mounted to the first and second ends 54 and 56 of the biasing member 52 are the rod-shaped tissue anchors 60. Tissue anchors 60 are rod-shaped members centrally mounted to the ends 54 and 56 respectively such that the longitudinal axes 63 of the anchors 60 are substantially perpendicular to the longitudinal axis 57 of biasing member 52. The biasing member 52 is seen to have a saw-tooth configuration.

Figure 4:
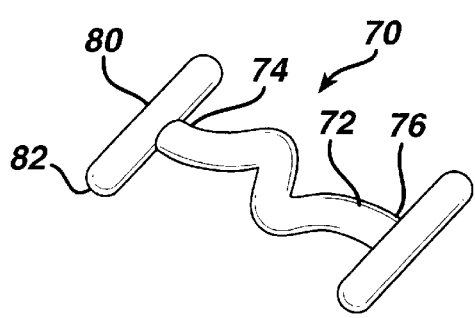
FIG. 4 is a perspective view of an H-type fastener of the present invention having a sinusoidal biasing section.
Figure 4A:
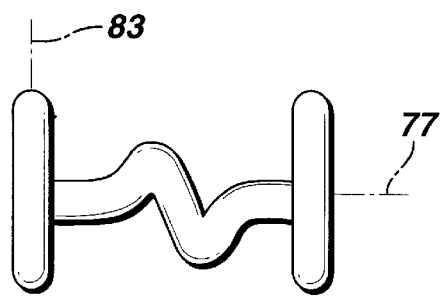
FIG. 4A is a side view of the H-type fastener of FIG. 4.

Another embodiment of an H-type fastener of the present invention is seen in FIGS. 4 and 4A. As seen in FIG. 4, the H-type fastener 70 is seen to have a central biasing section 72 having a sinusoidal configuration. Central biasing member 72 is seen to have first and second ends 74 and 76 respectively, and longitudinal axis 77. Mounted to the ends 74 and 76 of the member 72 are the rod-shaped tissue anchors 80. The rod-shaped tissue anchors 80 are seen to have longitudinal axes 83 and rounded ends 82. The tissue anchors 80 are mounted to the first and second ends 74 and 76 of biasing member 72 such that the longitudinal axes 83 of the anchors 80 are substantially perpendicular to the longitudinal axis 77 of the biasing member 72. As mentioned previously, the anchors may be mounted in a manner angulated with respect to each other or rotated with respect to each other.

Figure 5:
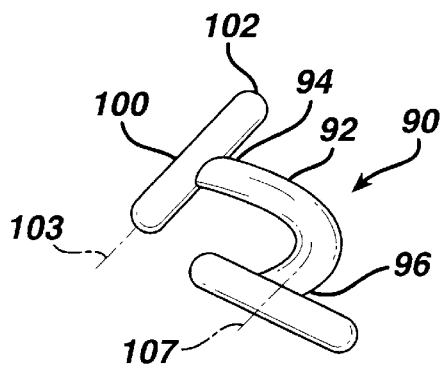
FIG. 5 is a perspective view of an H-type fastener of the present invention with a biasing section having a 90° arc-shaped configuration.
Figure 5A:
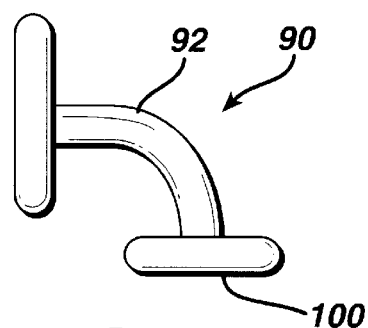
FIG. 5A is a side view of the H-type fastener of FIG. 5.
Figure 6:
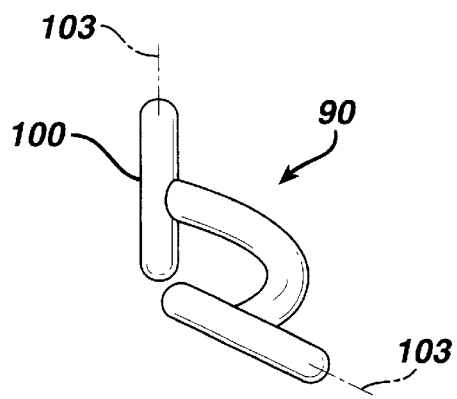
FIG. 6 is a perspective view of an H-type fastener of the present inventing with a biasing section having a 90° arc configuration, and end anchors which are rotated 90° with respect to each other.
Figure 6A:
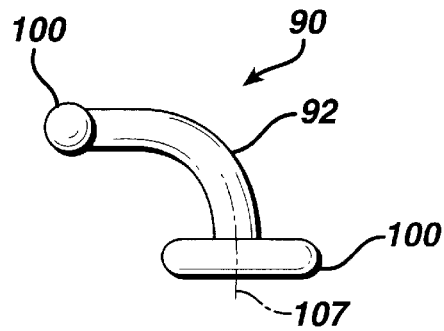
FIG. 6A is a side view of the H-type fastener of FIG. 6.

Yet another preferred embodiment of the H-type fasteners of the present invention is seen in FIGS. 5, 5A, 6, and 6A. Referring to FIG. 5, an anchor member 90 is seen to have central biasing section 92 having first and second ends 94 and 96 respectively. Central biasing member 92 is seen to have a curved configuration, e.g., substantially a 90 degree circular arc. As seen in FIG. 5A the tissue anchor members 100 are centrally mounted to the ends 94 and 96 of the biasing member 92 such that the longitudinal axes 103 and the longitudinal axis 107 are coplanar, although angulated with respect to each other. A variation of the H-type device 90 is seen in FIGS. 6 and 6A wherein the one tissue anchor member 100 is rotated with respect to the other such that the longitudinal axes 103 of tissue anchors 100 are no longer coplanar.

Figure 7:
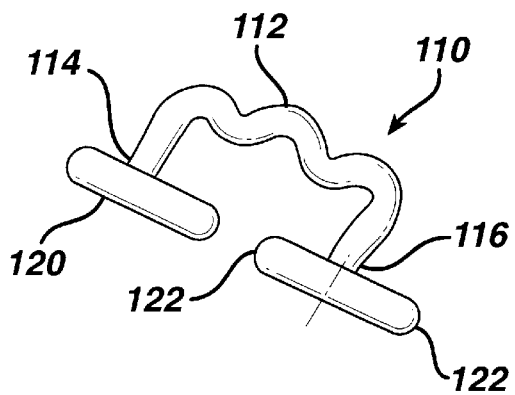
FIG. 7 is a perspective view of an H-type fastener of the present invention wherein the biasing section has a repeating sine wave configuration and also having the tissue anchors with longitudinal axes which are parallel to each other.
Figure 7A:
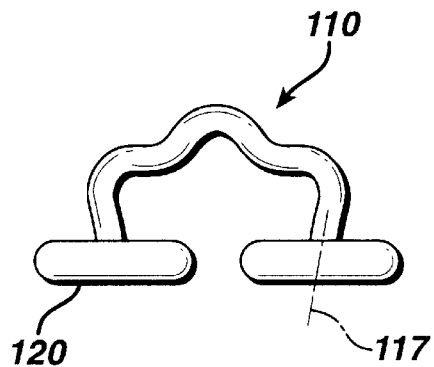
FIG. 7A is a side view of the H-type fastener of FIG. 7.

Yet another embodiment of the H-type fastener of the present invention is seen in FIG. 7. The fastener 110 is seen to have biasing section 112 having first end 114 and second end 116. Biasing section 112 has a repeating sinusoidal wave-like configuration. Tissue anchor members 120 are seen to be rod-shaped members having rounded ends 122 with longitudinal axes 123 and are seen to be centrally mounted to the ends 114 and 116 such that the central axes 123 of anchors 120 are substantially perpendicular to the ends 114 and 116.

Figure 8:
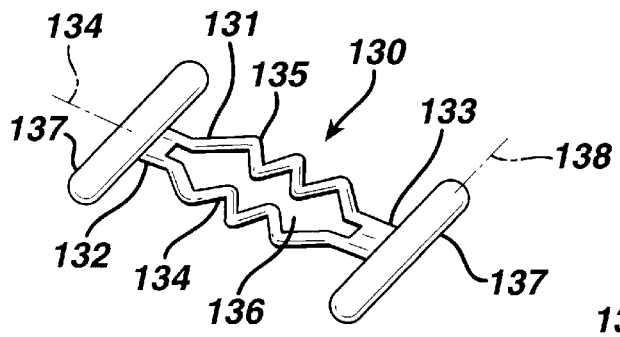
FIG. 8 is a perspective view of an H-type fastener of the present invention wherein the biasing section has two parallel sawtooth configurations separated by a central opening.
Figure 8A:
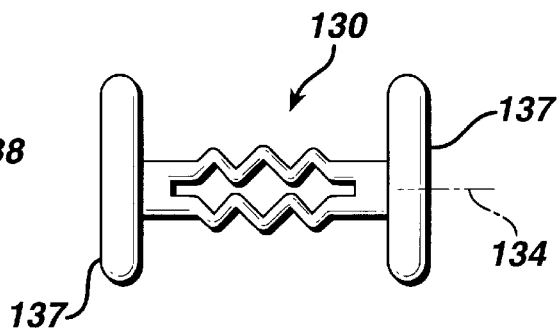
FIG. 8A is a side view of the H-type fastener of FIG. 8.

Another embodiment of the H-type fastener of the present invention is seen in FIG. 8. The H-type device 130 is seen to have central biasing member 131 having first and second ends 132 and 133 and longitudinal axis 134. The central biasing member 131 is seen to have opposed saw-toothed members 135 and central opening 136 separating the saw-toothed members 135. Mounted to the ends 132 and 133 of biasing member 131 are the rod-shaped members 137, having longitudinal axes 138 and rounded ends 139. The tissue anchors 137 may be mounted perpendicular to longitudinal axis 134 and may be coplanar or rotated with respect to each other so that they are not coplanar. Anchors 137 may be angulated with respect to each other.

Figure 9:
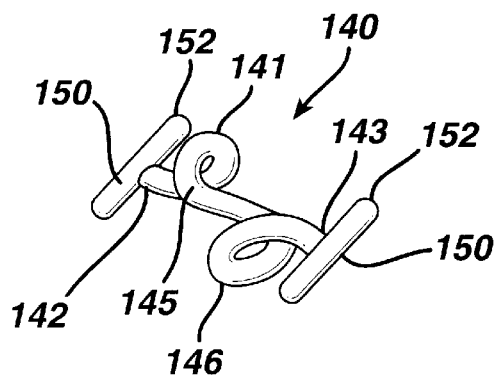
FIG. 9 is a perspective view of an H-type fastener of the present invention wherein the biasing section has a two adjoining loops.
Figure 9A:
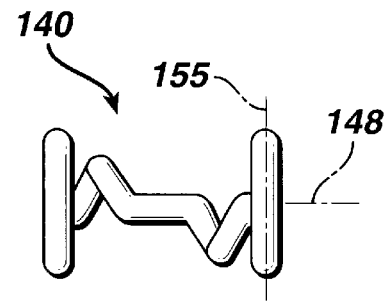
FIG. 9A is a side view of the H-type fastener of FIG. 9.
Figure 10:
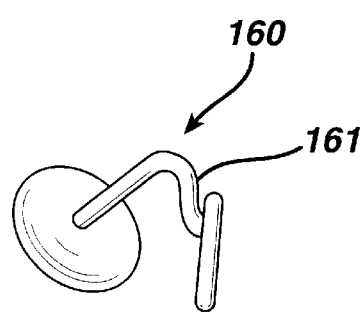
FIG. 10 is a perspective view of an alternate embodiment of an H-type fastener of the present inventing having a conventional straight central connecting section and V-shaped biasing tissue anchors mounted to the ends.
Figure 10A:
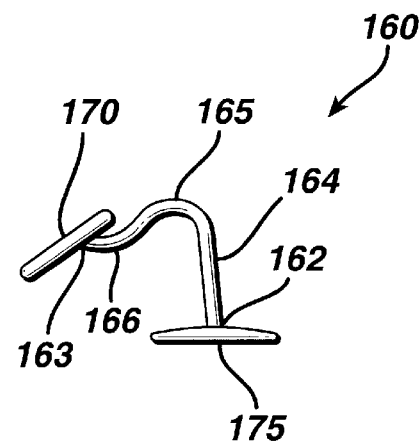
FIG. 10A is a side view of the H-type fastener of FIG. 15.

Yet another embodiment of the H-type fastener of the present invention is seen in FIGS. 9 and 9A. The fastener 140 is seen to have central biasing section 141 having double loops 145 and 146 and longitudinal axis 148. Biasing member 141 is also seen to have ends 142 and 143. Centrally mounted to the ends 142 and 143 are the rod-shaped tissue anchor members 150 having axes 155. The anchor members 150 are substantially perpendicular to the ends 142 and 143 and to longitudinal axis 148, but may be angulated with respect to each other. The tissue anchors 150 may be coplanar or may be rotated about axis 148 so that they are not coplanar Another embodiment of the H-type fastener of the present invention is seen in FIGS. 10 and 10A. The fastener 160 is seen to have central biasing section 161 having ends 162 and 163. The biasing member 161 is seen to have straight section 164, intermediate curved section 165, and curved section 166 adjacent to end 163. The tissue anchors that are attached to the ends 162 and 163 are seen to have different shapes. Rod-shaped tissue anchor member 170 is mounted to end 163 while disc-shaped member 175 is centrally mounted to end 162.

Figure 11:
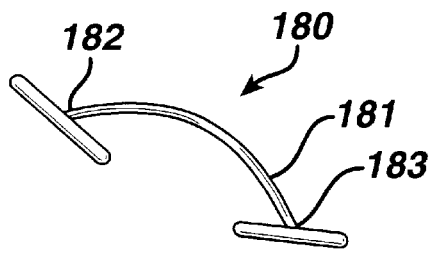
FIG. 11 is a perspective view of an H-type fastener of the present invention wherein the central biasing member is parabolically shaped.
Figure 11A:
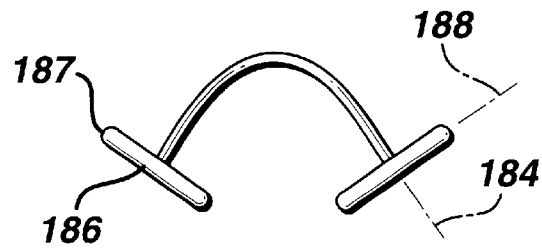
FIG. 11A is a side view of the H-type fastener of FIG. 11.

Still yet another embodiment of the H-type fasteners of the present invention is seen in FIGS. 11 and 11A. Fastener 180 is seen to have a parabolically shaped biasing section 181 having first and second ends 182 and 183 and longitudinal axis 184. Mounted to ends 182 and 183 in a manner as previously mentioned are the rod-shaped tissue anchor members 186 having curved ends 187 and longitudinal axes 188.

Figure 12:
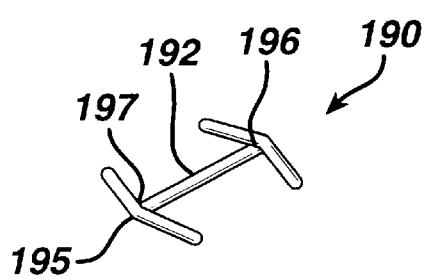
FIG. 12 is a perspective view of an H-type fastener of the present invention wherein one tissue anchor has a disk-like shape and the other anchor has a rod-like shape; the biasing member as an arc shaped section and a straight section.
Figure 12A:
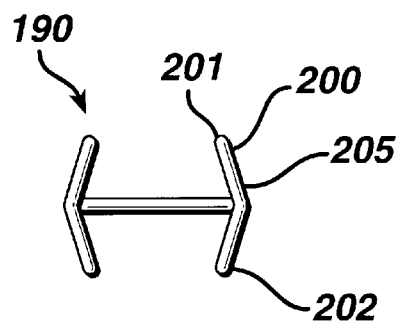
FIG. 12A is a side view of the H-type fastener of FIG. 12.
Figure 21:
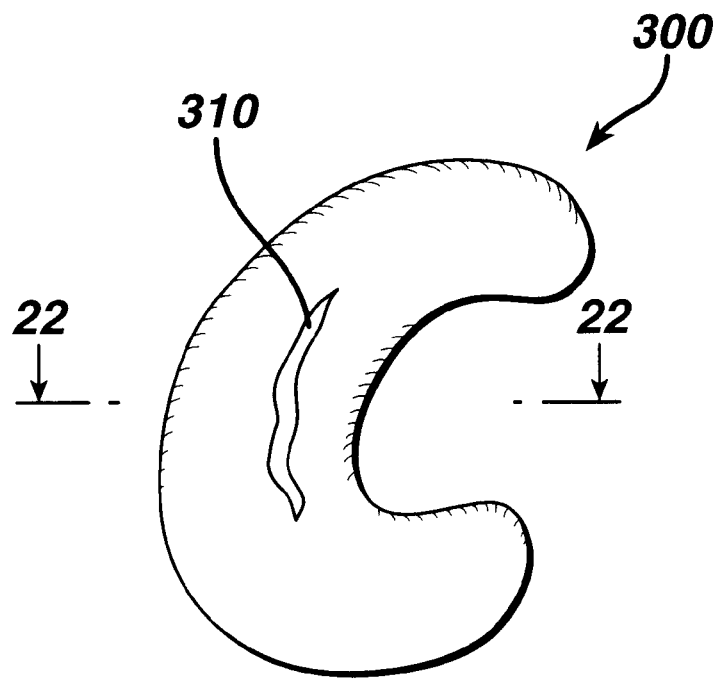
FIG. 21 is a top view of a meniscus having a tear.

Another embodiment of the H-type fastener of the present invention is seen in FIGS. 12 and 12A. The fastener 190 is seen to have a central connecting section 190 which is not a biasing member. Connecting section 190 has first and second ends 191 and 192, and longitudinal axis 195. Connecting section 190 preferably has a circular cross-section but may have any cross-section including those illustrated in FIGS. 13–20. Mounted to the ends 192 and 193 in a central manner are the biasing tissue anchors 200. Anchors 200 have legs 202 and 203 which are angulated with respect to each other and joined at an apex 205 to form a V-shaped structure. Legs 202 and 203 are seen to angulate inward toward member 190, but may be situated to angulate in the opposite direction. Anchors 200 may be rotated about axis 195 to be either coplanar or in different planes. Deflection of legs 202 and 203 outwardly away from member 192 from a first resting position to an extended or elastically deformed position will produce a biasing force on tissue retained between the anchors 200. Other shapes include U-shapes, a plurality of outwardly extending legs or appendages, inverted cone shapes, cylindrical shapes, X-shapes and other structural shapes as mentioned above for the no-biasing tissue anchors.

Those skilled in the art will appreciate that the configuration chosen for the central biasing member of the H-type fasteners of the present invention will depend upon several factors including, but not limited to, the magnitude of the biasing force required, the type of tissue to be approximated, the location within the body of the tissue or organ to be approximated, the size of the tear or incision in the tissue, whether absorbable or non-absorbable material is to be used to manufacture the devices, the material of construction, the type of surgical procedure, etc. It is within the purview of one skilled in the art to choose a final design after weighing these factors.

The central biasing members of the H-type fasteners of the present invention can have various cross sections as seen in FIGS. 13–20. Referring to FIG. 13, a cross-section of a preferred embodiment is seen wherein the cross-section 210 is a substantially circular cross-section. A substantially oval cross-section 215 is illustrated in FIG. 14. Illustrated in FIG. 15 is a substantially rectangular cross-section for a biasing member of the H-type fasteners of the present invention. Illustrated in FIG. 16 is a cross-section 220 comprising two square cross-sections 223 and 222 having diagonals 227 and 228 which are connected along the diagonals 227 and 228 at the corners 224 and 225. Illustrated in FIG. 17 is a cross-section consisting of two circles 232 and 233 attached tangentially along their circumferences at point 234.

Illustrated in FIG. 18 is a cross-section having central rectangular section 242 having ends 243 and 244 with circular sections 247 and 246 extending from ends 244 and 243. FIG. 19 illustrates a rectangular cross-section while FIG. 20 illustrates a cross-type or X-type cross-section having intersecting legs 265. It will be appreciated by those skilled in the art that equivalent cross-sections for the biasing member may be chosen. The central connecting members on the anchors of the present invention having biasing anchors such as seen in FIG. 12 may have similar cross-sections if desired.

The tissue anchor members useful on the H-type fasteners of the present invention can have various configurations including rods, disks, cones, spheres, and the like and equivalents thereof. The tissue anchor members may also be configured like structural members having openings therein such as an X-shaped member or a ring member having spokes, or an I-beam, T-beam, etc., and the like and equivalents thereof. In addition, although it is preferred that the anchor members are fixedly mounted to the biasing member or connecting member, the anchors may be rotatably mounted using conventional mounting configurations such as ball and socket joints, rivets, pins, snap rings, shafts, bushings, and the like and equivalents thereof.

Figure 22:
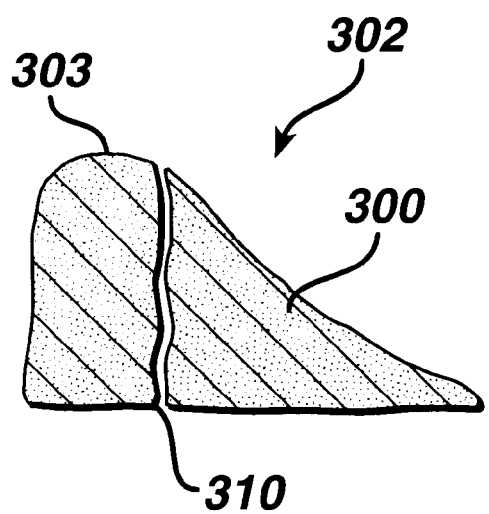
FIG. 22 is a cross-section of the meniscus of FIG. 21 along view line 22—22.
Figure 23:
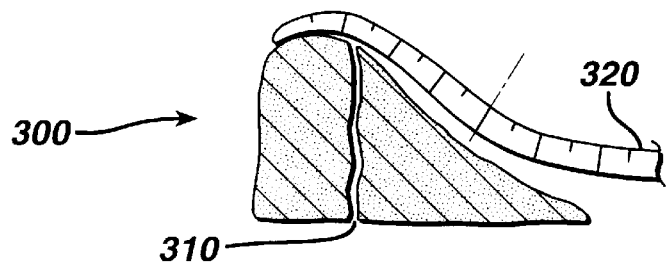
FIG. 23 illustrates an arthroscopic measuring device placed adjacent to the meniscus of FIG. 21.
Figure 24:
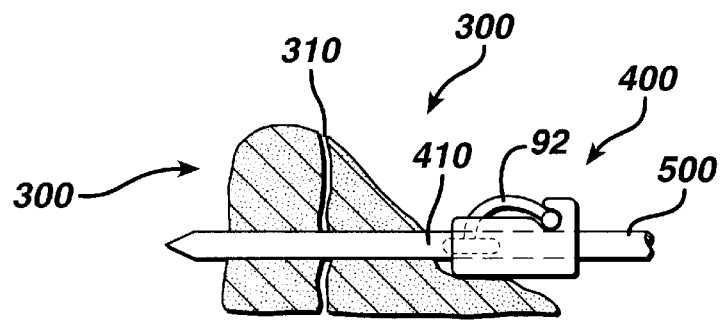
FIG. 24 illustrates a cross-sectional view of the meniscus having emplaced therein an insertion needle with an H-type fastener mounted in the insertion needle.
Figure 25:
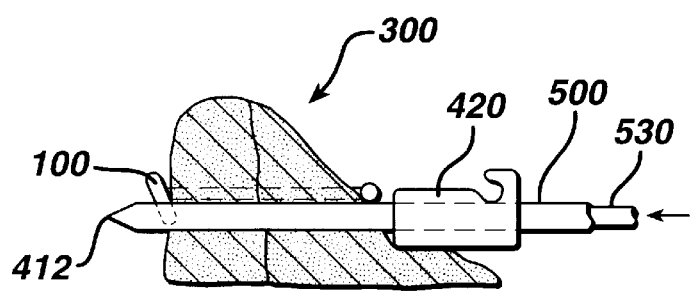
FIG. 25 illustrates the meniscus of FIG. 24 after the H-type fastener has been deployed from the insertion needle with the insertion needle still in place in the meniscus.
Figure 26:
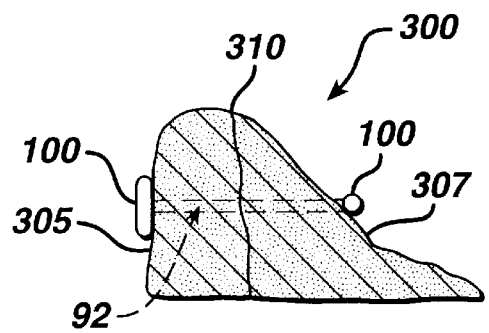
FIG. 26 illustrates the meniscus of FIG. 25 after removal of the insertion needle with the H-type fastener fully deployed in place about the tear in the meniscus, such that the tissue about the tear in the vicinity of the fastener is approximated by the biasing force of the central biasing section of the fastener.
Figure 27:
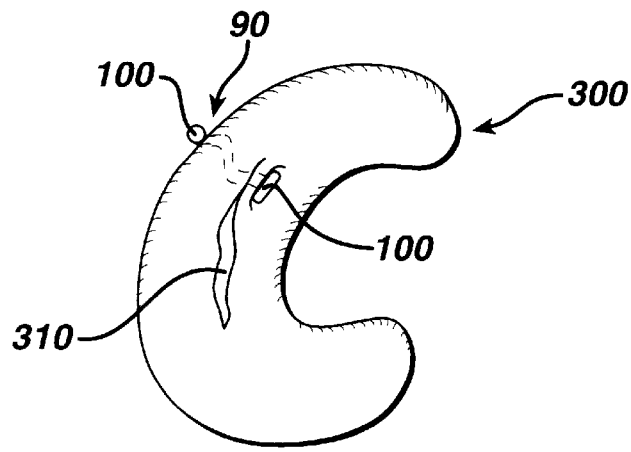
FIG. 27 is a top view of the meniscus of FIG. 26 illustrating the fastener deployed through the meniscus about the tear and causing the tear to be partially approximated.
Figure 28:
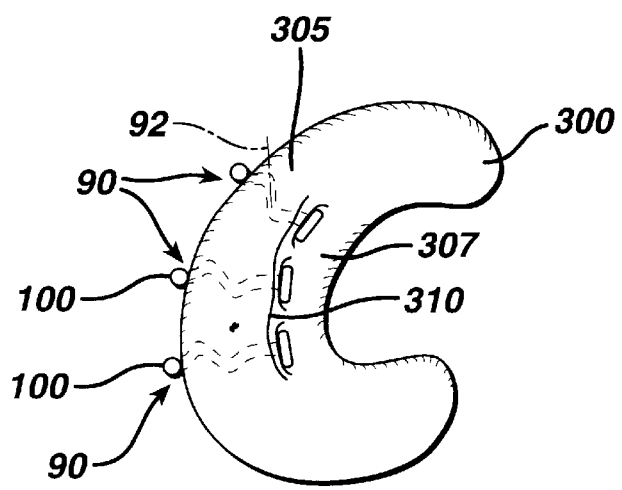
FIG. 28 is a top a top view of the meniscus of FIG. 27 after with multiple H-type fasteners have been deployed through the meniscus about the tear, thereby approximating the tissue about the tear.
Figure 29:
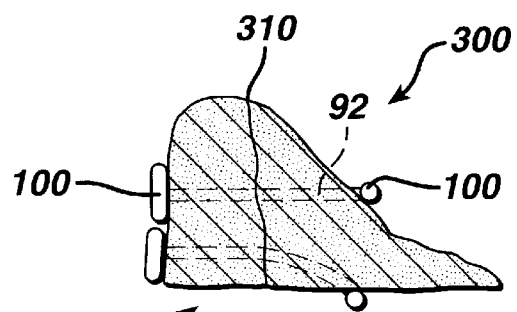
FIG. 29 is a cross-sectional view of the meniscus of FIG. 26 illustrating the deployment of an additional, supplemental H-type fastener placed above the fastener initially inserted to provide additional approximation in three dimensions.
Figure 30:
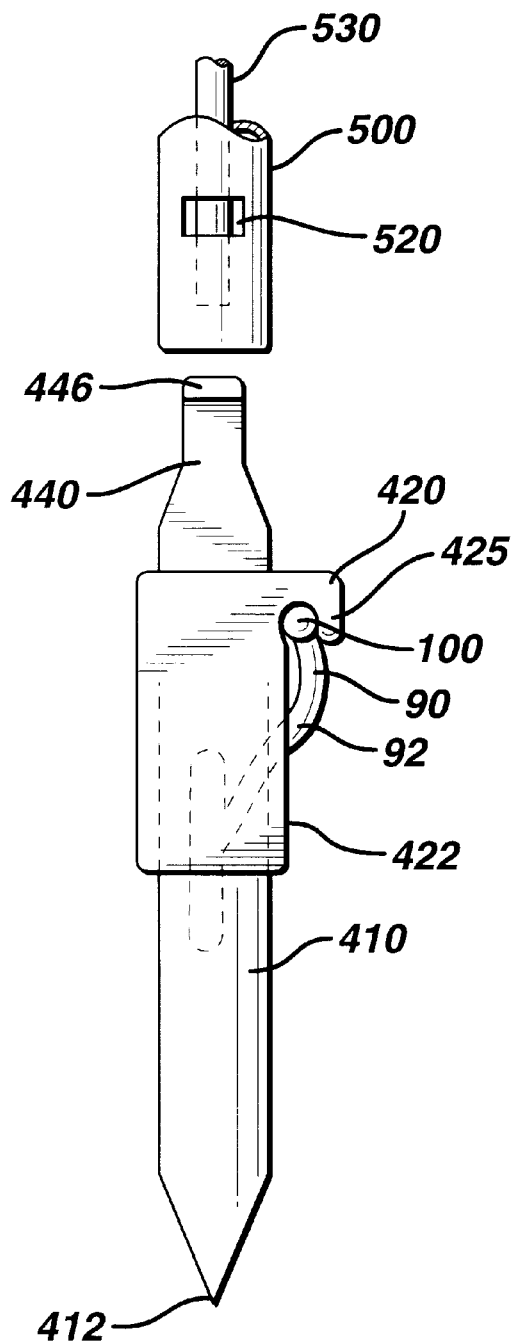
FIG. 30 illustrates an H-type fastener of the present invention mounted in an insertion needle.
Figure 31:
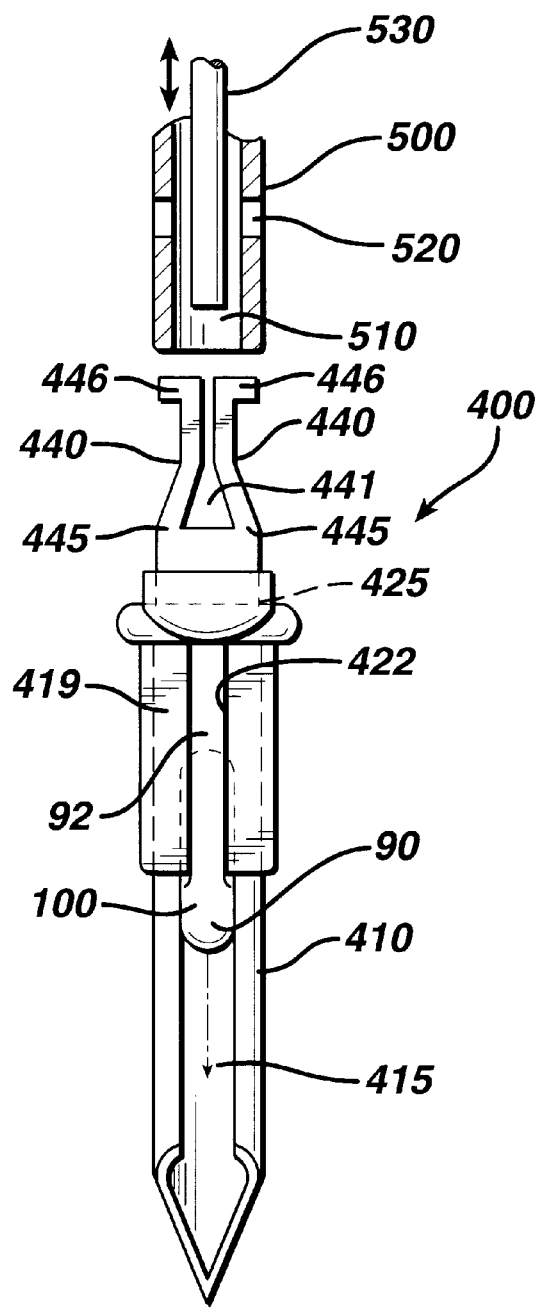
FIG. 31 illustrates a side view of the insertion needle of FIG. 30.

The H-type fasteners of the present invention can be utilized in many types of surgical procedures to approximate various types of mammalian tissue. The types of tissues which can be approximated include, but are not limited to, ligaments, cartilage, stomach tissue, intestinal tissue, muscle including skeletal muscle, cardiac muscle and involuntary muscle, bone, skin, nervous tissue, blood vessels and connective tissues. It is particularly preferred to use the H-type devices of the present invention to approximate cartilage. In particular, tears in cartilage such as that contained in the meniscus of the knee. The H-type fasteners of the present invention are typically utilized in the following manner. Referring to FIGS. 21–29, a meniscus 300 is seen to have a tear 310. The tear 31 is seen to extend from the top 302 of meniscus 300 to the bottom 303 as seen in FIG. 22. The size of the meniscus 300 may be measured using a conventional arthroscopic meniscal measuring device 320 with gradations 322 as seen in FIG. 23. Once the surgeon has measured the size of the meniscus 300, he is able to select an H-type fastener of the present invention which will properly approximate the tear 310 by exerting a biasing force on the tissue on either side of the tear 310. For example, fastener 90 of the present invention as illustrated in FIGS. 6 and 6A is loaded into a conventional H-type fastener insertion needle delivery device 400 as illustrated in FIGS. 30 and 31. The device 400 is seen to have distal needle cannula 410 having passageway 415, slot 417 in communication with passageway 415 and distal piercing point 412. Mounted to the proximal end 419 of cannula 410 is optional retainer collar 420. Collar 420 is seen to have slot 422 and hook member 425. Proximal leg locking members 440 are seen extend proximally from distal end 419 and are separated by space 441. Each leg has distal base section 445 forming a living hinge and proximal tab members 446. Device 400 is mounted to insertion cannula 500 by depressing the members 440 inwardly and inserting the proximal tab members into passage 510 and locking the tab members 446 in slots 520 contained in cannula 500. Device may similarly be removed form cannula 500 by depressing locking leg members 440 inwardly and thereby causing tab members 446 to dislodge form slots 520. Push rod 530 is seen to be slidably mounted in the passage 510 of cannula 500. H-type fastener 90 is loaded into device 400 by loading one tissue anchor 100 into cannula passageway 415 and the opposed anchor 100 into hook member 425, with biasing section 92 protruding through slots 417 and 422. Once the device 90 is loaded into the distal cannula 410 of delivery device 400, the surgeon then inserts the piercing point 412 through the meniscus 300 such that the needle cannula 410 travels through the meniscus and through tear 310. The surgeon then actuates the push rod 530 to push the tissue anchor member 100 through cannula 410 such that it is positioned adjacent to the surface 305 of meniscus 300. The surgeon then withdraws the needle cannula 410 thereby causing the other anchor 100 to be stripped from the anchor collar hook 425 and further causing biasing member 92 to be displaced from cannula 410 and causing the other anchor 100 to be positioned about the surface 307 of meniscus 300. The extended biasing member 92 exerts a biasing force upon anchors 100 thereby causing the anchors 100 to move inwardly with respect to each other thereby approximating the issue about tear 310. The procedure is repeated to insert additional H-members 90 until the entire tear 310 is approximated as seen in FIGS. 27–29. A similar surgical procedure can be performed in a similar manner utilizing H-type fasteners of the present invention having biasing tissue anchors such as the fastener illustrated in FIGS. 12 and 12A.

The following example are illustrative of the principles and practices of the present invention.

EXAMPLE

A patient was prepared for surgery and anesthetized using conventional procedures. Trocar cannulas were inserted into the capsule surrounding one of the patient's knees in accordance with standard arthroscopic procedures and a flow of saline was established to insufflate the joint. A conventional arthroscope was inserted into one cannula to visualize a tear in the patient's meniscus. After measuring the meniscus with a conventional meniscal measuring device, an appropriately sized H-type fastener of the present invention was mounted in a cannulated needle and inserted into a trocar cannula. The point of the needle was inserted through the meniscus and the needle was withdrawn, thereby placing the fastener in the meniscal tissue surrounding the tear and approximating a section of the tear. Two more fasteners were placed in the meniscus in the same manner thereby repairing the meniscal tear. The cannulas were then removed from the patient's knee and the trocar puncture wounds were approximated in a conventional manner.

The H-type fasteners of the present invention have many advantages. The fasteners facilitate tissue approximation in minimally invasive surgical procedures such as arthroscopic, endoscopic and laparoscopic procedures. The fasteners of the present invention apply a biasing force upon tissue which may facilitate healing. The fasteners are particularly useful in approximating tissue, especially tissue such as meniscal cartilage.

Although is invention has been shown and described with respect to detailed embodiments thereof, it will be understood by those skilled in the art that various changes in form and detail thereof may be made without departing from the spirit and scope of the claimed invention.

We claim:

1. An H-type fastener for tissue, comprising
 a central biasing member, said central biasing member having a first end, a second end, and a cross-section, said central biasing member capable of being elastically deformed from a first relaxed resting position to a second extended position;
 a first anchoring member mounted to the first end of the biasing member; and,
 a second anchoring member mounted to the second end of the biasing member,
 wherein the cross-section comprises a pair of squares, each square having corners and a diagonal, the squares connected to each other at one of said corners along the diagonal.

2. An H-type fastener for tissue, comprising
 a central biasing member, said central biasing member having a first end, a second end, and a cross-section, said central biasing member capable of being elastically deformed from a first relaxed resting position to a second extended position;
 a first anchoring member mounted to the first end of the biasing member; and,
 a second member mounted to the second end of the biasing member, wherein the cross-section comprises a pair of circles having circumferences connected at one point about their circumferences.

3. An H-type fastener for tissue, comprising an elongated central connecting member, said elongated central connecting member having a first end, a second end, and a cross-section;

a first anchoring member mounted to the first end of the connecting member, said first anchoring member capable of being elastically deformed from a first relaxed resting position to a second extended position; and, a second anchoring member mounted to the second end of the connecting member, said second anchoring member capable of being elastically deformed from a first relaxed resting position to a second extended position, wherein the anchoring members have a V-shaped configuration comprising two angulated legs connected at an apex and wherein the apex of each anchoring member is mounted to an end of the elongated central connecting member.

* * * * *